United States Patent [19]
Fontirroche et al.

[11] Patent Number: 5,820,594
[45] Date of Patent: *Oct. 13, 1998

[54] BALLOON CATHETER

[75] Inventors: Carlos A. Fontirroche, Miami Springs; Stephen J. Querns, Boca Raton, both of Fla.

[73] Assignee: Cordis Corporation, Miami Lakes, Fla.

[*] Notice: The term of this patent shall not extend beyond the expiration date of Pat. No. 5,538,510.

[21] Appl. No.: 673,392

[22] Filed: Jun. 28, 1996

Related U.S. Application Data

[63] Continuation-in-part of Ser. No. 189,209, Jan. 31, 1994, Pat. No. 5,538,510.

[51] Int. Cl.⁶ ................................................. A61M 29/00
[52] U.S. Cl. ........................ 604/96; 604/265; 606/194
[58] Field of Search ................................. 604/265, 280, 604/281, 282, 283, 93, 264, 266, 96; 606/192–198

[56] References Cited

U.S. PATENT DOCUMENTS

| | | |
|---|---|---|
| 3,814,137 | 6/1974 | Martinez . |
| 4,923,450 | 5/1990 | Maeda et al. . |
| 4,994,047 | 2/1991 | Walker et al. . |
| 5,063,018 | 11/1991 | Fontirroche et al. . |
| 5,120,323 | 6/1992 | Shockey et al. . |
| 5,195,969 | 3/1993 | Wang et al. ............................... 604/96 |
| 5,195,971 | 3/1993 | Sirhan . |
| 5,221,270 | 6/1993 | Parker ..................................... 604/282 |
| 5,270,086 | 12/1993 | Hamlin . |
| 5,272,012 | 12/1993 | Opolski ................................... 604/265 |
| 5,290,306 | 3/1994 | Trotta et al. . |
| 5,538,510 | 7/1996 | Fontirroche et al. ................... 604/265 |

FOREIGN PATENT DOCUMENTS

| | | |
|---|---|---|
| 0420488 | 4/1991 | European Pat. Off. . |
| 2130093 | 5/1984 | United Kingdom . |
| 2209121 | 5/1989 | United Kingdom . |

OTHER PUBLICATIONS

Quantun—Plexar—Tie–Layer Resins The Essential Bond For Coextruded Packaging, 8 pages.

Quantum—Plexar—The–layer Resin—Designing Plexar Tie–Layer Resins With Low MVTR Properties, 4 pages.

Quantum—Plexar—Tie–Layer Resin—Evaluation of Plexar Tie–Layers for EVOH/PET Coextrusion, 2 pages.

Brochure of unknown date from Schneider Innovation For Life—2 pages.

Article by Norman G. Gaylord et al. entitled: "Maleation of Linear Low–Density Polyethylene by Reactive Processing" —Gaylord Research Institute, New Providence, NJ, pp. 1941–1949.

Article by Norman G. Gaylord entitled: "Compatibilizating Agents: Structure and Function in Polyblends" J. Macromol. Sci—Chem., A26 (b), pp. 1211–1229 (1989), Research Institute for Scientist–Emeriti, Drew University, Madison, NJ.

*Primary Examiner*—Ronald Stright, Jr.
*Attorney, Agent, or Firm*—Michael W. Montgomery

[57] ABSTRACT

The intravascular balloon catheter has an elongated shaft defining an inflation lumen and a guidewire lumen, as well as a balloon disposed near the distal end of the shaft. The inflation lumen communicates with and provides pressurized inflation fluid to the interior volume of the balloon, and the guidewire lumen is adapted to slidingly receive a guidewire. The shaft is formed of a length of flexible plastic tube, and the inner surface of the guidewire lumen is lined with an inner plastic layer. The plastic materials of the outer tube and inner layers are different, and they may be chemically bonded to each other.

7 Claims, 1 Drawing Sheet

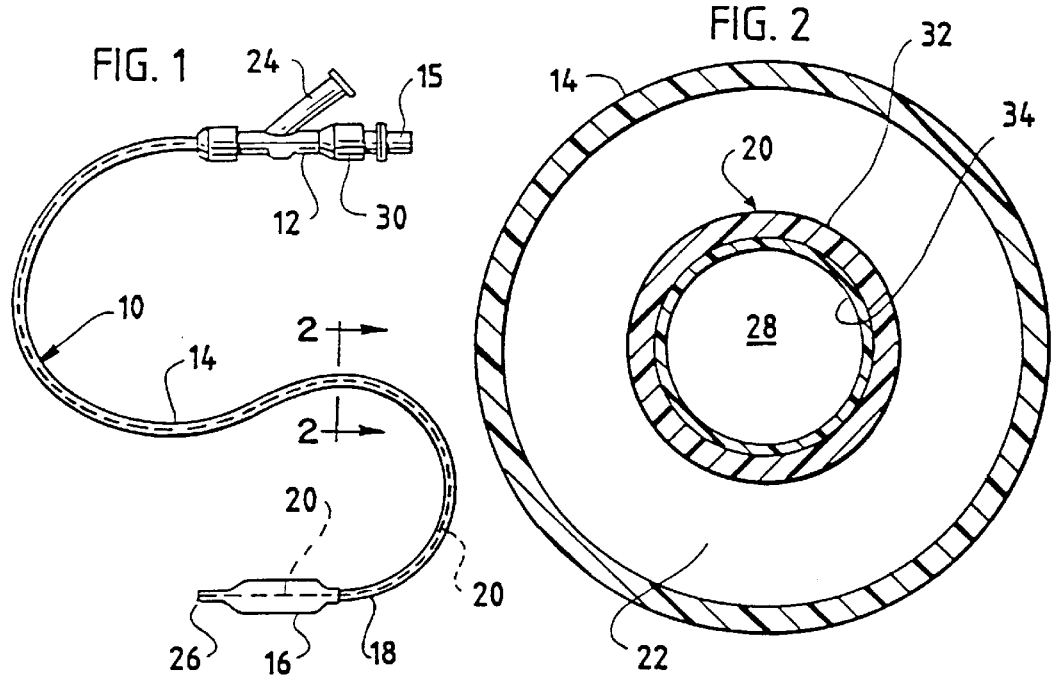
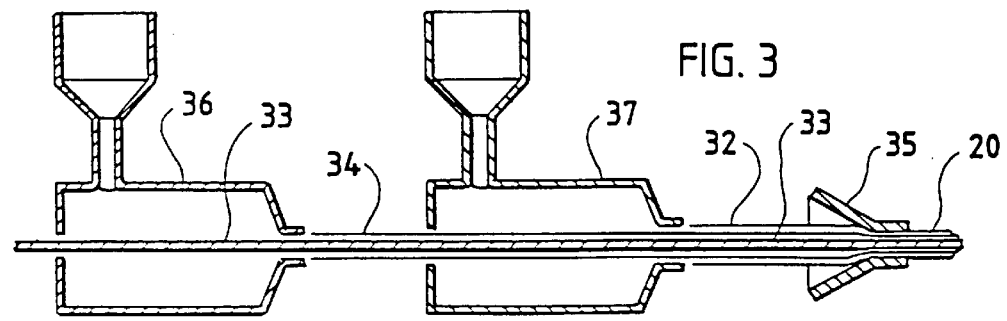
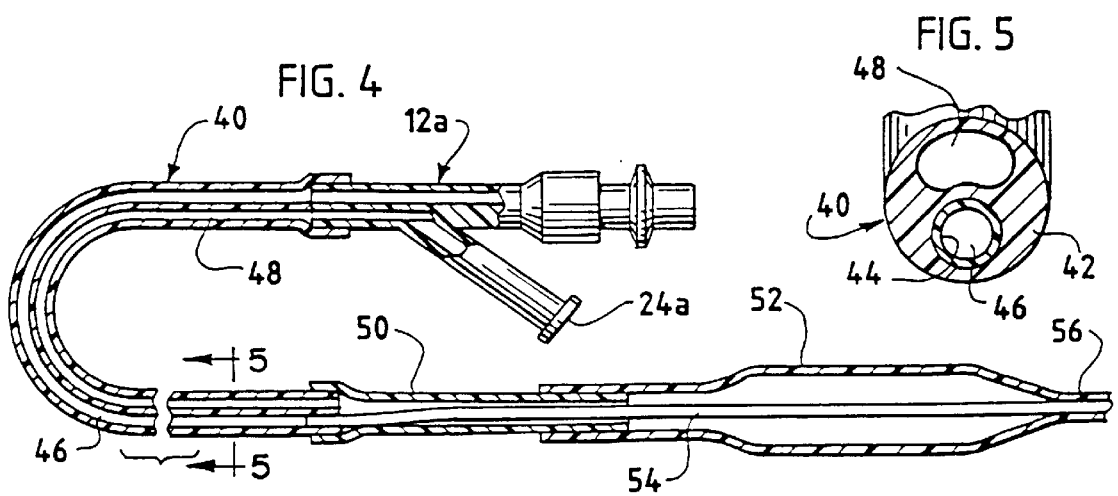

BALLOON CATHETER

BACKGROUND AND DESCRIPTION OF THE INVENTION

This is a continuation-in-part of application Ser. No. 08/189,209, filed on Jan. 31, 1994 now U.S. Pat No. 5,538,510.

This invention relates generally to the field of intravascular catheters, and more particularly to a balloon catheter having coextruded tubing.

Intravascular catheters, such as catheters for advancement into the blood vessels of a patient, are presently in wide clinical use. Many clinical applications exist for such catheters, including diagnostic and interventional procedures. Examples of such procedures are coronary angiography and angioplasty, the latter of which is known as percutaneous transluminal coronary angioplasty (PTCA). Of course, the present invention may be utilized in any application to which it is suitable.

Intravascular catheters are generally constructed of an elongate tubular shaft having proximal and distal ends, and defining one or more passages or lumens. It is desirable to construct the catheter shaft to increase its ability to advance through the various twists and turns of the vascular system, so that a physician can readily guide the distal tip of the catheter to a desired position. Accordingly, the catheter shaft should have selected flexibilities along portions of its length so that it can bend to follow or track the desired path, referred to as trackability. The catheter should exhibit sufficient axial stiffness or pushability to traverse the desired distance along that path. And the catheter shaft should resist twisting, or transmit torque, from its proximal to the distal end. This characteristic is referred to as torqueability, and can assist the physician to select a desired path with a catheter having a shaped distal tip by twisting the catheter proximal end.

For example, in the particular case of an angioplasty catheter, an angioplasty balloon or other interventional device may be provided at the catheter distal end to expand or dilate blockages in blood vessels. These blockages consist of a narrowing of the blood vessel called a stenosis. The balloon is often made of a flexible, inelastic material designed to expand along a predetermined curve to precise diameters at particular pressures. This type of expansion curve performance enables the balloon to impose pressures of several atmospheres to expand the stenosis without becoming too large. After the balloon has been expanded to temporarily compresses the stenosis, the balloon catheter is then deflated and removed from the patient, allowing improved blood flow through the vessel.

It is further desirable to provide the catheter guidewire lumen with a low friction or lubricious inner surface, which will allow the catheter to be advanced along a guidewire using less force, and so that a guidewire or inner catheter can more easily pass through the guidewire lumen. Conventionally, a catheter shaft may be made of nylon, low density polyethylene, polyurethane, or polyethylene terephthalate (PET), but the friction coefficients for such materials may be considered too high for some applications. The inner surface of the guidewire lumen may be provided with a lubricious coating such as a silicone, but such coatings may not sufficiently adhere to the catheter material. Such coating processes are also particularly difficult with small diameter intravascular catheters. Moreover, silicone resins and other coatings generally lack the best low-friction characteristics to facilitate relative movement between a guidewire and an intravascular catheter.

An alternative to a coating is a separate inner tube, usually made of preformed polytetrafluoroethylene (PTFE). The PTFE tube may be installed within the catheter shaft by sliding it into place and then shrinking the catheter shaft around it. This inner PTFE sleeve provides the desired low friction characteristic to the guidewire lumen, while the balance of the catheter shaft can provide other desired qualities. However, PTFE is a relatively stiff plastic material. It has sometimes been found that the presence of the PTFE tubing can make the catheter shaft too stiff, and the catheter may be more susceptible to kinking when the catheter turns a sharp corner in the vascular system of the patient. As is well known, PTFE bonds only with great difficulty to most other plastic materials. As a result, the PTFE does not bond in any significant way to the nylon or PET outer catheter shaft, and the PTFE inner tubing may consequently shift with respect to the outer catheter shaft.

Other polymers having low surface friction include high density polyethylene (HDPE). However, HDPE is also incompatible with other materials commonly used for catheter body, for example nylon. Additionally, HDPE does not form a significant bond with nylon upon coextrusion of a nylon outer catheter body and a HDPE inner layer or sleeve. Such a HDPE sleeve can also slip in its relative position within the catheter shaft, even after coextrusion, due to the absence of a substantial bond.

The novel balloon catheter design of the present invention has a composite catheter shaft incorporating inner and outer tubular layers of different plastic materials which are bonded to each other for firm retention and ease of manufacture. The desired bond between the materials of the balloon catheter shaft may be achieved by coextruding the inner and outer tubular layers. The inner layer material is selected to provide the desired low friction characteristic, while the outer shaft material is selected for the purpose of optimizing catheter shaft performance. The resulting composite shaft structure provides the desired catheter performance characteristics, including flexibility, pushability, and torque transmission. The balloon catheter of the present invention thus achieves the desired lubricious liner, the advantageous firm bond between the inner and outer catheter layers, and the other desired performance characteristics of the balloon catheter.

Because the inner plastic layer defines a catheter lumen having the desired low friction characteristic, the selection of the desired outer plastic layer materials for the catheter may be greatly broadened to optimize catheter performance. For instance, a material may be selected which bonds optimally to the desired balloon material of the balloon catheter. The material of the outer plastic layer preferably has a greater stiffness than the material of the inner plastic layer, to provide the balloon catheter a shaft which has both bending flexibility and yet axially stiff enough for optimal "pushability" for advancement into the vascular system of a patient. For example, nylon, polyurethane, or PET may be selected for the outer plastic layer.

In contrast, the material of the inner plastic layer may be a selected vinylic polymer having functional groups bonded to the material of the outer plastic layer. The vinylic polymer may be a copolymer, having a major amount of ethylene units and a minor unit amount of unsaturated carboxylic acid or an anhydride thereof. Typically, known resins manufactured and sold by the Quantum Chemical Company under the trademark Plexar may be used for the inner plastic layer. These materials are vinylic, for example polyethylene of varying densities, polypropylene, or polyethylene vinyl acetate, which are copolymerized with a small amount of maleic acid. These materials have previously been used as "tie layers" for multilayer plastic sheeting, the Plexar material being an inner layer which bonds together dissimilar outer plastic layers. Other unsaturated carboxylic acids such as fumaric acid, cinnamic acid, crotonic acid, linoleic acid, or the like may also be used as a substitute for maleic acid.

In accordance with this invention, a plastic material similar to Plexar or the like may be used as typically the inner layer of a multiple layer catheter tubing, taking advantage of that material's relatively good chemical bonding characteristic. Preferably the functional plastic material is not used to bond two dissimilar layers together, but rather making use of the material in its own right for its desired characteristics'. For example, high density polyethylenes which have been copolymerized with a minor amount of functional groups such as an unsaturated carboxylic acid or an anhydride thereof may be used to provide a firm bond with an outer layer of nylon, PET, or polyurethane for example, while providing a low friction surface to the catheter lumen. Specifically, the inner plastic layer may comprise a vinylic polymer having one to five mole percent of maleic anhydride polymer units, copolymerized preferably with ethylene to provide a high density polyethylene having low friction characteristics.

The catheter tubing of this invention may be simply coextruded as a multiple tubular layer catheter, with the reactive polymer used in this invention being typically the innermost layer. That innermost layer will preferably become chemically bonded during the coextrusion to an outer plastic layer which is made of a different material. Thus, normally incompatible plastic materials may be bonded together in the catheter tubing of the present invention to provide both a firm bond and the desired characteristics of the respective materials selected.

For example, nylon and high density polyethylene are normally quite sealingly incompatible with each other. By this invention, a high density polyethylene copolymer serving as an inner catheter tubing layer may be firmly covalently bonded to a nylon outer catheter layer, so that the nylon can provide desired stiffness to the catheter while still permitting flexibility, and the high density polyethylene inner layer can provide low friction to a guidewire or inner catheter. The chemical bonding between the two catheter layers can take place during the extrusion process, or, if desired, subsequent heat treating or the like may be provided.

Alternate embodiments of the present balloon catheter may be constructed of coaxial tubes defining the inflation and guidewire lumens as shown in FIG. 1, or a "dual lumen" parallel configuration shown in FIG. 5, or a combination thereof as illustrated in FIG. 4. Of course, the balloon catheter of the present invention may also be provided with drug delivery or infusion capability, by forming small apertures in the balloon or by constructing the catheter shaft with a third lumen communicating between a proximal infusion port and a distal infusion aperture. Moreover, an alternative embodiment of the balloon catheter may be designed to enable blood to flow between a point proximal from the inflated balloon and a point distal to the balloon, thereby perfusing while the balloon temporarily blocks a blood vessel.

The balloon and catheter shaft may also encompass various designs. For example, the guidewire tube and guidewire lumen may be disposed outside of the balloon. Or the guidewire tube may be affixed to and extend along the wall of the balloon.

In addition, it is often desirable to exchange one catheter that has been advanced over a guidewire with another catheter, without dislodging the guidewire from the site for treatment. Accordingly, the present balloon catheter may be constructed in a rapid exchange configuration, in which the guidewire lumen extends from the distal tip of the catheter only to a guidewire port between the balloon and the proximal hub.

By this invention, an intravascular catheter is provided which includes a length of flexible plastic tubing, having an outer plastic layer and an inner plastic layer These layers are made of different plastic materials. Preferably, a chemical bond of the covalent type is formed between the outer and inner plastic layers of the catheter shaft tubing. The flexible plastic tubing of this invention is easily coextruded, to provide a catheter tubing with a lubricious inner lumen but that requires no separate PTFE or other low friction tube or coating. The balloon catheter exhibits the desired performance characteristics of pushability, trackability, and flexibility, yet also facilitates easy advancement of a guidewire through the guidewire lumen of the catheter. The overall cost to manufacture the balloon catheter of this invention is thereby reduced, while the performance of the catheter is improved.

These and various other objects, advantages and features of the invention will become apparent from the following description and claims, when considered in conjunction with the appended drawings.

BRIEF DESCRIPTION OF THE DRAWINGS

FIG. 1 is a perspective view of a balloon catheter in accordance with this invention;

FIG. 2 is an enlarged cross-sectional view of the catheter of FIG. 1, along line 2—2;

FIG. 3 is a schematic view of the process for extruding catheter tubing in accordance with this invention;

FIG. 4 is a longitudinal cross-sectional view of an alternative embodiment of a balloon catheter in accordance with this invention; and FIG. 5 is an enlarged transverse cross-sectional view, along line 5—5 of FIG. 4.

DETAILED DESCRIPTION OF SPECIFIC EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

With reference to the drawings, the balloon catheter of the present invention is generally designated by reference numeral 10. Balloon catheter 10 has a Y-connector or hub 12, a catheter shaft constructed of an outer tubular body 14 and an inner tubular body 20, and a dilatation balloon 16. The hub 12 is disposed at the proximal end 15 of balloon catheter 10, while the balloon 16 is near the distal end of catheter 10. Balloon 16 is formed of a flexible, substantially inelastic material, having a cylindrical dilatation section as well as a proximal leg and a distal leg. Outer tubular body 14 is coupled with hub 12 at proximal end 15, and the distal end 18 of outer body 14 is likewise connected to the proximal leg of balloon 16. Outer tubular body 14 terminates at the point where it is sealed to the proximal end of balloon 16. The outer surface of outer tube 14 may of course be treated to improve the performance of the balloon catheter 10, such as by applying a hydrophillic or other type of coating.

Inner tubular body 20 extends through the interior of outer catheter tube 14, defining a generally annular space or inflation lumen 22 between outer catheter tube 14 and inner catheter tube 20. Inflation port 24 of hub 12 communicates in conventional manner with the proximal end of inflation lumen 22. Inflation lumen 22 extends along the catheter between catheter tubes 14 and 20, and terminates in communication with the interior of balloon 16. Inner catheter tube 20 extends from proximal hub 12 through the length of outer tube 14 and through the interior volume of balloon 16. The distal end 26 of inner tube 20 is sealed to balloon 16 such that the distal end of an inner lumen 28 defined by inner catheter tube 20 is open. A guidewire port 30 of hub 12 communicates with guidewire lumen 28 of inner catheter tube 20, to enable fluid communication throughout the entire length of the catheter from proximal end 15 through the open distal end 26 of inner catheter tube 20, extending through balloon 16. A guidewire (not shown) may thus be more easily advanced and withdrawn through guidewire lumen of balloon catheter 10, to assist in directing its distal tip into selected vessels or to temporarily provide greater stiffness or support the catheter shaft.

In accordance with the present invention, balloon catheter 10 incorporates the novel arrangement of an improved catheter shaft having multiple plastic layers. The performance of the catheter can thus be optimized to increase its pushability, trackability, flexibility, torqueability, and the lubricity of the guidewire lumen. As illustrated in the drawings, the catheter shaft consists of a length of flexible plastic tube which, in turn, includes an outer plastic layer 32 and an inner plastic layer 34. The plastic materials of the outer and inner layers 32 and 34 are made of different materials that are chemically bonded to each other. While that specific multi-layer plastic tube is illustrated as inner catheter tube 20 in this specific embodiment, it could be used for the outer catheter tube 14 as well. As an alternative, a bonding plastic layer could be placed both inside and outside of a catheter having a nylon middle layer, for example.

Outer tubular plastic layer 32 of catheter tube 20 may preferably be selected from the group consisting of nylon, polyurethane, and polyester, with such materials typically being of greater stiffness than the material of inner tubular plastic layer 34. Outer plastic layer 32 may typically comprise about 60 to 90 percent of the overall wall thickness of tube 20, providing a desired amount of stiffness to the tube while tube 20 retains a thin wall.

The material of inner tubular plastic layer 34 is preferably made of a material which exhibits lower frictional characteristics than the material of outer plastic layer 32. This low friction surface facilitates the advancement of a guidewire or a separate, smaller catheter, for example, through the catheter of this invention, while at the same time enjoying the benefit of the physical properties provided to the catheter by the presence of and the physical properties of outer tubular layer 32.

Accordingly, for an angioplasty or angiography catheter, the overall catheter may exhibit a desired level of stiffness while still remaining flexible, due to the combined properties of inner and outer catheter tubes 20 and 14. At the same time, the frictional characteristics of the walls of lumen 28 may remain low irrespective of the frictional characteristics of layer 32. Furthermore, this may be accomplished without the separate addition of a PTFE sleeve, a coating, or the like in the catheter lumen, which requires a complexity in the manufacturing process. The layers of inner catheter tube 20 can be simply coextruded.

The material of the inner plastic layer 34 is preferably no more than half the overall thickness of the wall of inner catheter tube 20, and it may be as low as about 5 or 10 percent of the overall thickness if desired. The material of inner plastic layer 34 is preferably a copolymer of a major amount of a vinylic polymer such as ethylene and a minor amount of an unsaturated carboxylic acid or an anhydride thereof, for example, a polyethylene which contains about 1 to 5 mole percent of maleic anhydride polymer units present in the molecule, on a mole percent basis.

More specifically, the material of inner plastic layer 34 may be a high density polyethylene, modified for example with the presence of about 1 or 2 mole percent of copolymerized maleic and anhydride units. As previously stated, such modified polyethylene resins are commercially available from the Quantum Chemical Corporation under the trademark Plexar, being used conventionally as tie layer resins for the bonding of dissimilar plastics together in coextruded films. However, nonreactive materials may be used for the inner layer 34 when coextrusion provides a physical bond of adequate strength with layer 32. Specific extrusion conditions for the best bonding depend on the product used.

In this invention, however, such materials as Plexar resins may be used in their own right as the second layer of this invention, to coat a layer of a catheter on the inside thereof to achieve the advantages previously described herein.

The functional groups which are found on the vinylic polymers used in this invention to promote a chemical bond between the outer and inner plastic layers may include copolymerized units such as an unsaturated carboxylic acid, or an anhydride thereof, or functional groups which are substituents of vinyl-containing molecules, polymerized or co-polymerized to form the vinylic polymer, for example hydroxyl in the case of polyvinyl alcohol, or other pendant reactive groups as may be desired to permit the formation of a chemical bond between two plastic materials.

The copolymerized, unsaturated carboxylic acid or anhydride thereof thus can serve as a functional group which bonds a vinylic polymer of the inner layer to the plastic of the outer layer. For example, particularly when the first layer is a polyamide such as nylon or another nitrogen-containing polymer such as polyurethane, this can be effectively accomplished. Similarly, such vinylic polymers having acid functional groups may react with hydroxyl-containing polymers of the outer layer, under proper reaction conditions. Such reactions may take place during co-extrusion of the two layers, to form a covalent bond between the outer and inner plastic layers of the catheter tube as it is formed by the extrusion.

Preferably, inner plastic layer 34 is about 0.0005 to 0.003 inch thick while outer plastic layer 32 is about 0.003 to 0.006 inch thick, preferably giving a total wall thickness for the inner catheter tube 20 of 0.005 to 0.008 inch. The overall diameter of inner catheter tube 20 is typically about 0.02 to 0.035 inch. Outer catheter tube 14 has a typical wall thickness of about 0.003 to 0.005 inch, and a typical diameter of 0.04 to 0.05 inch, to provide a generally inflation lumen 22, although it is understood that inner tube 20 is unconstrained and will not remain in exactly coaxial relationship with outer catheter tube 14.

Inner catheter tube 20 may be coextruded in generally conventional manner as schematically illustrated in FIG. 3. Extruder dies 36 and 37 bring cylindrical streams of molten plastic which are to form the outer layer 32 and inner layer 34 into coaxial, physical contact around mandrel 33, to pass through extruder die 35 while molten, to form catheter tube 20. During this process, the reactive moieties of the plastic formulation which includes inner layer 34 forms chemical bonds with the plastic of outer layer 32. Specifically, the nylon plastic of outer layer 32 is believed to react by forming amide-like linkages with the maleic anhydride units of the high density, copolymerized polyethylene plastic of layer 34 to form a strong bond between the layers. Then, the manufactured tube 20 may be assembled in conventional manner to form the catheter of this invention, as disclosed herein.

High density polyethylene is generally understood by those skilled in the art to have a density of at least about 0.94 g/cc. For purposes of this invention a polyethylene containing reactive groups and being of this density or greater is defined to be "high density polyethylene."

Referring to FIGS. 4 and 5, another embodiment of an intravascular balloon catheter in accordance with this invention is disclosed. A catheter having the conventional hub 12A similar to hub 12 is connected to the proximal end of double lumen tube 40, which may be manufactured by an extrusion process similar to that disclosed in U.S. Pat. No. 5,063,018 to Fontirroche, which is commonly assigned with the present application, the disclosure of which is incorporated herein by reference. In accordance with the present invention, that extrusion process must of course be modified to coextrude the tube 40 disclosed herein. Tube 40 is formed of an outer layer or body 42, plus an inner layer 44 which may be added by coextrusion, typically in lumen 46, through which the guidewire extends.

The side arm 24a of hub 12a communicates with the other lumen 48 of tube 40. The distal end of tube 40 is sealed to a second length of flexible plastic tube 50 which may be made of nylon or the like to have sufficient stiffness characteristics. Inner tubular layer 44 may be made of a material similar to inner tubular layer 34 of the previous embodiment for similar purposes. The outer catheter layer 42 may be similar to outer catheter layer 32 of the previous embodiment although possibly not of a material of greater stiffness than the material of layer 44 since the mass of material 42 in cross section is relatively greater. Basically the inventive principles described above still hold.

The material of layer 42 is relied upon to provide desired stiffness to the catheter. The material of layer 44 provides desired low frictional characteristics to lumen 46, both of these being provided in a single catheter by a coextrusion process.

Tube 50 connects at its distal end to a catheter balloon 52. Lumen 48 communicates with the interior of balloon 52 through tube 50, communicating at the proximal end of lumen 48 with side arm 24a of the hub.

An inner catheter tube 54 is sealed to the distal end of lumen 46 and extends proximally through balloon 52 to be also sealed to the balloon at the distal catheter end 56. Tube 54 may be similar in structure to tube 20 of the previous embodiment, having an inner layer and an outer layer analogous to layers 32, 34 to perform the desired functions thereof as described above.

Thus, various different embodiments of a catheter are disclosed which may be of a desired stiffness and having a desired sealing compatibility to a catheter balloon 16 or 52, for example. At the same time, a catheter lumen similar to lumen 28 or 46 may have a low friction inner surface made of a different material that is bonded, and preferably covalently bonded, to the plastic of tube 32 or 42.

It should be understood that an unlimited number of configurations for the present invention can be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

We claim:

1. An intravascular balloon catheter, comprising:

a flexible balloon disposed near a distal end of the catheter; and a flexible catheter shaft defining an inflation lumen and a guidewire lumen, the inflation lumen providing fluid communication between an inflation port and the interior of said balloon, and the guidewire lumen adapted to slidingly accept a flexible guidewire and extending from a proximal guidewire port to a distal guidewire port;

a portion of said catheter shaft incorporating a flexible plastic tube defining said guidewire lumen, said tube having an outer plastic layer and an inner plastic layer, said inner plastic layer being formed of a copolymer of a major amount of high density polyethylene and a minor amount of an unsaturated carboxylic acid or an anhydride thereof, the material of said outer plastic layer being selected from the group consisting of nylons polyurethane, and polyester;

wherein the inner plastic layer exhibits lower surface friction than the outer plastic layer, the plastic materials of said outer and inner plastic layers being different, and chemically bonded to each other in direct and continuous contact.

2. The intravascular balloon catheter as set forth in claim 1, further comprising a proximal hub coupled with a proximal end of the catheter shaft, said inflation port being disposed in the proximal hub.

3. The intravascular balloon catheter as set forth in claim 1, wherein the proximal guidewire port is disposed between the balloon and a proximal end of the catheter shaft, and the distal guidewire port is disposed distal to the balloon.

4. The intravascular balloon catheter as set forth in claim 1, wherein the flexible plastic tube defining said guidewire lumen extends along most of the length of said catheter.

5. The intravascular balloon catheter as set forth in claim 1, wherein the balloon is formed of a substantially inelastic material.

6. The intravascular balloon catheter of claim 1, in which the material of the outer plastic layer has greater stiffness than the material of the inner plastic layer.

7. An intravascular balloon catheter, comprising:

a first flexible plastic tube defining a guidewire lumen, said first tube being coextruded of an outer plastic layer and an inner plastic layer, the plastic materials of said outer and inner plastic layers being different and bonded to each other, said guidewire lumen being adapted to slidingly receive a guidewire, wherein the material of said inner plastic layer includes at least a majority of high density polyethylene, said material of the inner plastic layer being more flexible and exhibiting a more lubricious surface than the material of said outer plastic layer, and the material of said outer plastic layer being selected from the group consisting of nylon, polyurethane, and polyester;

a second flexible plastic tube surrounding said first tube and defining an inflation lumen between the outer surface of the first tube and the inner surface of the second tube; and a flexible balloon having a distal end coupled to said first tube and a proximal end coupled to said second tube, such that the interior volume of the balloon is in fluid communication with said inflation lumen.

* * * * *

UNITED STATES PATENT AND TRADEMARK OFFICE
Certificate

Patent No. 5,820,594                          Patented: October 13, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Carlos A. Fontirroche, Miami Springs, FL; Stephen J. Querns, Boca Raton, FL; and Thomas N. Trotta, Miami Beach, FL.

Signed and Sealed this Thirteenth Day of December 2005.

NICHOLAS D. LUCCHESI
*Supervisory Patent Examiner*
Art Unit 3763